United States Patent [19]

Tegeler et al.

[11] Patent Number: 4,602,035
[45] Date of Patent: Jul. 22, 1986

[54] ANTIDEPRESSANT (3-ARYL-2,3-DIHYDROBENZOFURAN-3-YL)ALKYLAMINES

[75] Inventors: John J. Tegeler, Bridgewater, N.J.; Craig J. Diamond, North Walls, Pa.; Grover C. Helsley, Pottersville, N.J.

[73] Assignee: Hoechst-Roussel Pharmaceuticals Inc., Somerville, N.J.

[21] Appl. No.: 559,134

[22] Filed: Dec. 7, 1983

[51] Int. Cl.⁴ .................. A61K 31/34; C07D 307/81
[52] U.S. Cl. .................. 514/469; 549/304; 549/467; 564/316; 558/388; 558/408
[58] Field of Search .................. 549/467; 424/285; 514/469

[56] References Cited

U.S. PATENT DOCUMENTS

| | | | |
|---|---|---|---|
| 2,513,698 | 7/1950 | Weston et al. | 549/304 |
| 3,103,520 | 9/1963 | Zaugg et al. | 549/467 |
| 3,156,688 | 11/1964 | Zaugg et al. | 549/467 |
| 3,467,675 | 9/1969 | Petersen et al. | 549/467 |

FOREIGN PATENT DOCUMENTS

| | | |
|---|---|---|
| 627839 | 8/1949 | United Kingdom . |
| 1526331 | 9/1978 | United Kingdom . |

OTHER PUBLICATIONS

Weston et al., J. Am. Chem. Soc., vol. 74, pp. 653-656, (1952).

Petersen et al., Acta. Pharmacol. et Toxicol., vol. 24, pp. 121-133 (1966).

Burger's Medicinal Chem., 4th Ed. (Part III), Wiley and Sons, pp. 847-848 (1979).

*Primary Examiner*—Henry R. Jiles
*Assistant Examiner*—Bernard I. Dentz
*Attorney, Agent, or Firm*—Tatsuya Ikeda

[57] ABSTRACT

There are described compounds of the formula

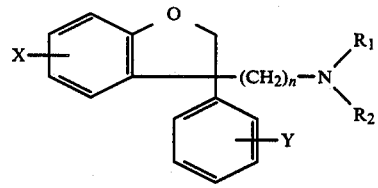

where n is 2 or 3, X and Y are each independently hydrogen, loweralkyl, or halogen, and $R_1$ and $R_2$ are each independently hydrogen, loweralkyl, cyano, beta,-beta,beta-trichloroethyoxycarbonyl, cyclopropylmethyl, phenethyl, or cyanoethyl, but at least one of the two is loweralkyl, which are useful as antidepressant and analgesic agents; novel intermediate compounds for preparing said compounds; and methods for synthesizing the foregoing compounds.

29 Claims, No Drawings

ANTIDEPRESSANT (3-ARYL-2,3-DIHYDROBENZOFURAN-3-YL)ALKYLAMINES

This invention relates to compounds of the formula

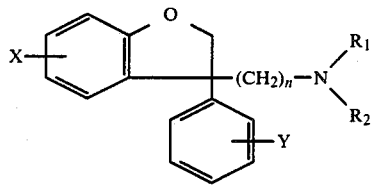
(I)

where n is 2 or 3, X and Y are each independently hydrogen, loweralkyl, or halogen, and $R_1$ and $R_2$ are each independently hydrogen, loweralkyl, cyano, beta,-beta,beta-trichloroethyoxycarbonyl, cyclopropylmethyl, phenethyl, or cyanoethyl, but at least one of the two is loweralkyl, or a pharmaceutically acceptable acid addition salt thereof, which are useful as antidepressant and analgesic agents, antidepressant compositions comprising an effective depression alleviating amount of a compound of Formula I; and analgesic composition comprising an effective amount of a compound of Formula I.

This invention also relates to compounds of the formula

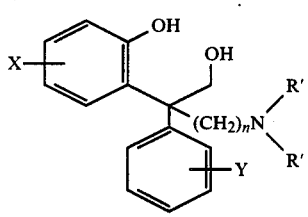
(II)

where n is 2 or 3, X and Y are each independently hydrogen, loweralkyl or halogen, and R' is loweralkyl which are useful as intermediates for synthesizing compounds of Formula I.

This invention also relates to compounds of the formula

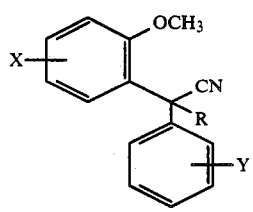
(III)

where X and Y are each independently hydrogen, loweralkyl or halogen, and R is hydrogen or —(CH$_2$)$_n$N(R')$_2$, n being 2 or 3 and R' being loweralkyl which are useful as intermediates for synthesizing compounds of Formula II.

This invention also relates to methods of synthesizing the foregoing compounds of Formulas I, II and III.

To the best of our knowledge the compounds of the present invention have not been described or suggested.

Throughout the specification and appended claims, the term "loweralkyl" shall mean an alkyl group having 1–4 carbon atoms. The term "halogen" shall mean fluorine, chlorine, bromine or iodine unless otherwise indicated.

The compounds of this invention can be prepared by following one or more of the steps described below. Throughout the description of the synthetic steps, the definitions of n, X, Y, $R_1$, $R_2$, R and R' are as given above unless otherwise indicated.

STEP A

Compound VI below is prepared by reacting Compound IV with Compound V in a suitable solvent such as dry THF.

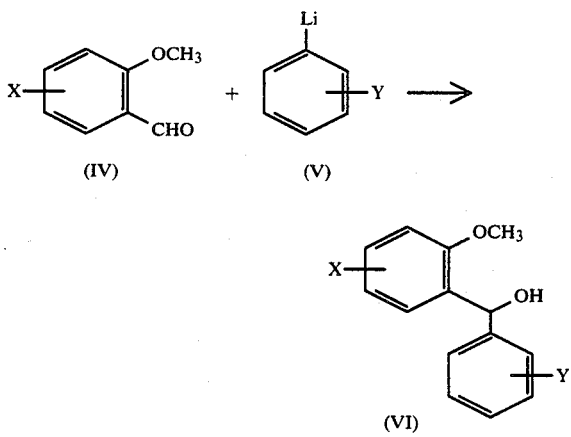

Compound IV is readily available or synthesizable by known methods. For instance, where X is 5-chloro in Formula IV, it can be prepared by reacting o-anisaldehyde with N-chlorosuccimide in a suitable solvent such as DMF. A typical reaction condition is stirring at 60° C. for 20 hours.

Compound V can be prepared in situ by reacting, for instance, Compound VII with n-BuLi in a suitable solvent such as THF. A typical

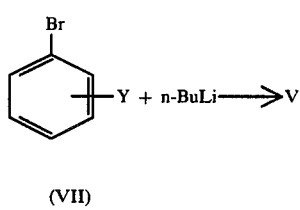

reaction condition is adding a suitable solution of n-BuLi (such as hexane solution) at a low temperature (e.g. −60° C.) under nitrogen and stirring the mixture for a few hours.

After Compound V has been prepared in situ as described above, a suitable solution of Compound IV (e.g. THF solution) is added to the above mixture and the mixture is stirred, for instance, at room temperature overnight to obtain Compound VI.

STEP B

As an alternative to STEP A, Compound VI can be prepared by using a Grignard reagent of Formula VIII instead of Compound V.

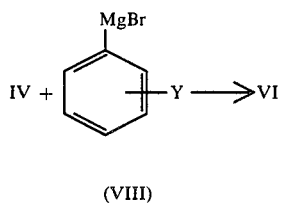

(VIII)

Said Grignard synthesis is conducted in a routine manner in a suitable solvent such as anhydrous ethyl ether.

STEP C

Compound VI is chlorinated to Compound IX by use of, for instance, thionyl chloride in a suitable solvent such as chloroform or dichloromethane. A typical reaction condition is refluxing the mixture for a few hours.

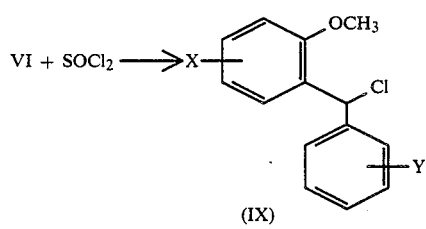

(IX)

STEP D

Compound IX is reacted with AgCN in a suitable solvent such as dry $CH_3CN$ to afford Compound X. A typical reaction condition is refluxing the mixture for 5-30 hours.

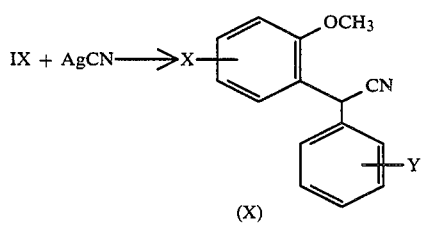

(X)

STEP E

Where the oxime compound of Formula XI below is readily available or synthesizable as in the case of X=Y=hydrogen in said formula, Compound X can also be obtained, instead of following the above STEPS A through D, by reacting Compound XI with trifluoroacetic anhydride, for instance, in a suitable solvent such as dichloromethane. A typical reaction condition is stirring the reaction mixture at room temperature for a few hours.

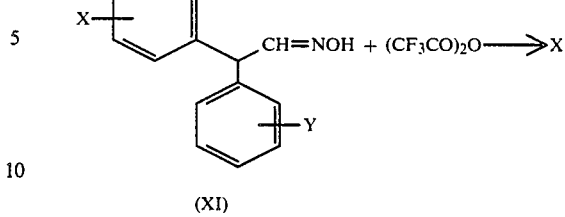

(XI)

STEP F

Compound of Formula IIIa below is obtained by reacting Compound X with a compound of Formula XII where Hal is chlorine or bromine and n is 2 or 3.

$$X \;+\; Hal-(CH_2)_nNMe_2 \longrightarrow$$

(XII)

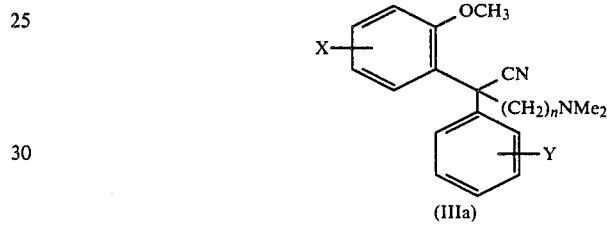

(IIIa)

Said reaction is conducted with the aid of a strong base such as $LiN(i-Pr)_2$. Said lithium compound is prepared in situ, for instance, by reacting n-BuLi with di-isopropylamine in a suitable solvent. Thus, said synthesis of Compound IIIa is conducted typically as follows.

A solution of n-BuLi in hexane is added to a solution of di-isopropylamine in dry THF at −70° C. under nitrogen and the mixture is stirred for 15 minutes and then brought to −30°. A solution of Compound X in THF is added to the above mixture and the resultant mixture is stirred at 0°-30° C. for less than 1 hour. Compound XII is added dropwise to the resultant mixture at 0° C. and the mixture is thereafter stirred at room temperature for a short period of time (e.g. 15 minutes) and then at reflux for a few hours to obtain Compound IIIa.

STEP G

Compound IIIa is cyclized in a strongly acidic medium such as 48% HBr to afford Compound XIII. A typical reaction condition is stirring the mixture at 100° C. for 40 hours.

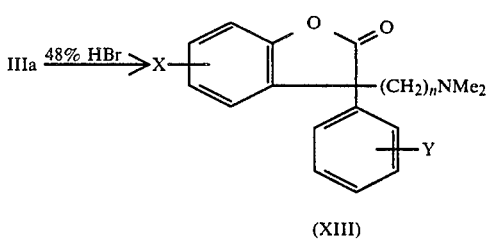

(XIII)

STEP H

Compound XIII is subjected to hydride reduction to afford Compound IIa by use of, for instance, LiAlH₄ in a suitable solvent such as anhydrous ethyl ether. A typical reaction condition is stirring the reaction mixture at 0°–30° C. for 1–3 hours.

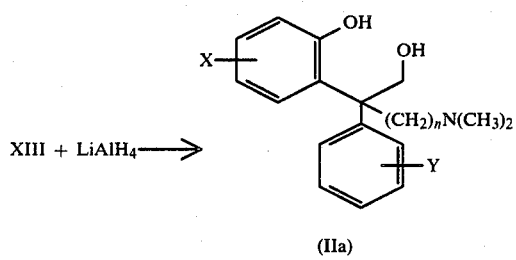

(IIa)

STEP I

Compound IIa is cyclized to afford Compound Ia by reacting it, for instance, with a mixture of methanesulfonyl chloride and triethylamine in a suitable solvent such as dichloromethane. A typical reaction condition is stirring the mixture at 0°–30° C. for a few hours.

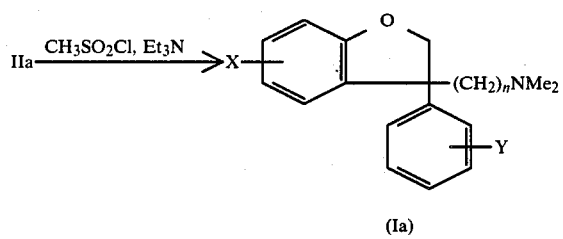

(Ia)

STEP J

Compound Ia is reacted with cyanogen bromide or chloride, preferably bromide, in a suitable solvent such as chloroform to afford Compound XIV. A typical reaction condition is refluxing the mixture for several hours.

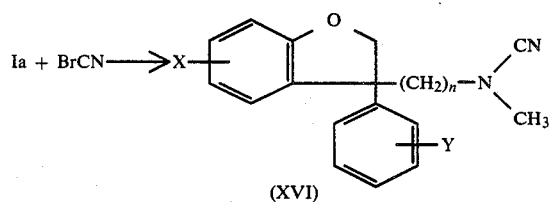

(XVI)

STEP K

Compound Ia is reacted with beta,beta,beta-trichloroethyl chloroformate in a suitable solvent such as dichloromethane in the presence of an acid scavenger such as K₂CO₃ to afford Compound XV. A typical reaction condition is stirring the mixture at room temperature overnight.

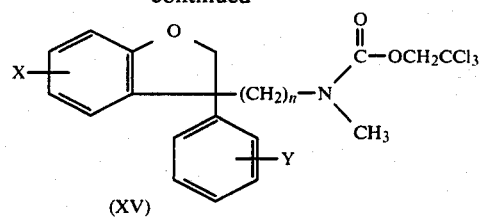

(XV)

STEP L

Compound XV is reacted with zinc and glacial acetic acid to afford Compound XVI. Typically, activated zinc is added in small portions to a solution of Compound XV in glacial acetic acid and the mixture stirred at room temperature for a few hours.

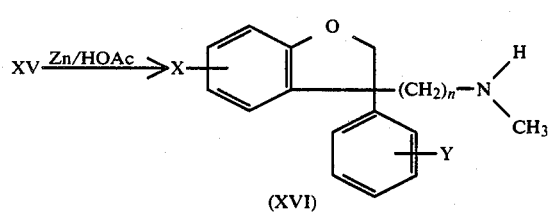

(XVI)

STEP M

Compound XVI is reacted with cyclopropylmethyl chloride in a suitable solvent such as DMF in the presence of an acid scavenger such as K₂CO₃ and a reaction initiator such as KI to afford Compound XVII. A typical reaction condition is stirring the mixture at 65° C. for several hours.

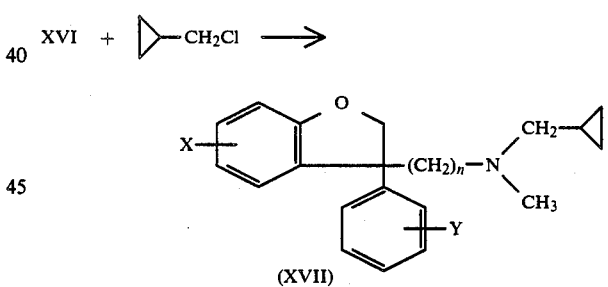

(XVII)

STEP N

As an alternative to STEP M, Compound XVI may first be reacted with cyclopropanecarboxylic acid chloride to obtain the corresponding amide, and the the amide may be reduced to afford Compound XVII above. The first step (amidation) is conducted, for instance, in dichloromethane in the presence of pyridine and stirring the mixture at room temperature overnight. The second step (reduction) is conducted, for instance, by reacting the amide with LiAlH₄ in a suitable solvent such as dry THF and stirring the mixture at room temperature for about 1 hour.

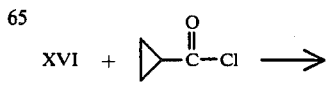

-continued

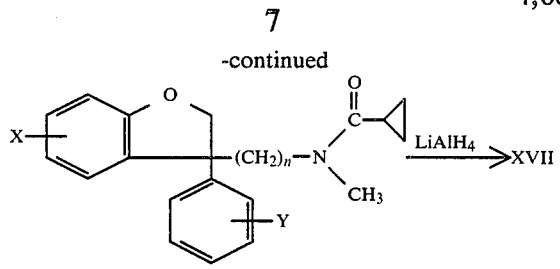

STEP O

Compound XVI is reacted with phenethyl bromide to afford Compound XVII. Said alkylation reaction is conducted, for instance, in DMF in the presence of $K_2CO_3$ and KI, and stirring the mixture at 80° C. for 4 hours.

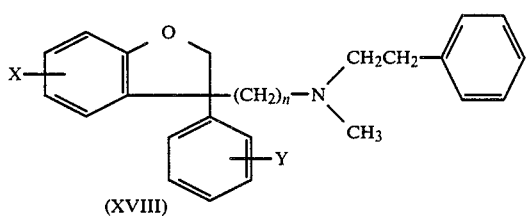

(XVIII)

STEP P

Compound XVI is reacted with acrylonitrile to afford Compound XIX. Said reaction is conducted, for instance, by using an excess amount of acrylonitrile and stirring the mixture of the two reactants at room temperature for a few hours and then at 75° C. for a few hours.

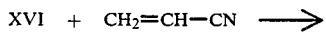

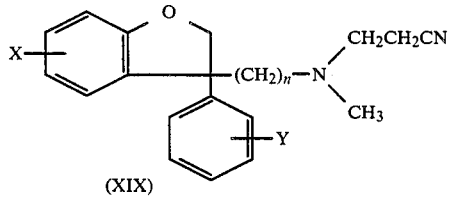

(XIX)

It will be noticed that the foregoing STEPS A through P are directed to the synthesis of Compounds I where at least one of $R_1$ or $R_2$ is methyl, to the synthesis of Compounds II where R' is methyl and to the synthesis of Compound III where R is hydrogen or $(CH_2)N.NMe_2$. However, it will be apparent from the foregoing descriptions of the synthetic scheme that the remaining compounds covered by Formulas I, II and III can be prepared in a similar manner by using a compound of the formula $Hal-(CH_2)_nN(R_3)_2$ where $R_3$ is an alkyl group of 2-4 carbon atoms instead of Compound XII in STEP F and following the subsequent STEPS G through P.

All other starting materials shown above are either known compounds or easily prepared by routine methods known to the art from readily available materials.

Compounds I of the present invention are useful as antidepressant agents due to their ability to prevent Tetrabenazine induced ptosis in mice. The method used is as follows.

Male mice weighing 20 to 30 grams are used in test groups of five subjects. All compounds are dissolved, or suspended with one drop of a non-ionic surfactant in distilled water and administered in volumes of 10 ml/kg of body weight. Tetrabenazine (TBZ) solution is made from methanesulfonate salt and the concentration is adjusted to enable the administration of 40 mg/kg of base by intraperitoneal injection (i.p.).

If the test compound is administered intraperitoneally, TBZ is injected 30 minutes after administration. If the test compound is administered orally (p.o.), TBZ is injected 60 minutes after the administration. A control group receives solvent and TBZ by the same route and at the same intervals as the drug groups.

Thirty and sixty minutes after TBZ injection the subjects are placed in individual plastic containers ($10\frac{1}{2}"\times 8"\times 6"$) and one minute after transfer they are scored for ptosis on the following scale: eyes closed=4, eyes $\frac{3}{4}$ closed=3, eyes $\frac{1}{2}$ closed=2, eyes $\frac{1}{4}$ closed=1, and eyes open=0. The total score for each group of five will therefore be from 0 to 20 and these scores are used as indications of drug activity.

The vehicle-control group score is used as a determinate of the validity of each test. If the control score is less than 17, the results are discarded and the test repeated.

For $ED_{50}$ estimation, four or five doses are administered in order to bracket the estimated value and only vehicle-control scores of 17 to 20 are accepted to assure the accuracy of the $ED_{50}$ estimate. A linear-regression analysis is used to estimate $ED_{50}$ values. Results of the antidepressant activities of some of the compounds of this invention are shown in Table 1.

The compounds of the invention compare favorably with the well known antidepressant compound imipramine, which, in a similar test exhibited an antidepressant $ED_{50}=5.5$ mg/kg, orally.

Compounds I of the present invention are also useful as analgesic agents due to their ability to alleviate pain in mammals. The activity of the compounds is demonstrated in the 2-phenyl-1,4-benzoquinone-induced writhing test in mice, a standard assay for analgesia, [Proc. Soc. Exptl. Biol. Med., 95, 729 (1957)]. Results of the analgesic activities of some of the compounds of this Invention are shown in Table 1.

The compounds of the invention compare favorably with the well known analgesic compound ibuprofen, which, in a similar test exhibited an analgesic $ED_{50}=10.4$ mg/kg, orally.

TABLE 1

| | TBZ | | PQW | |
|---|---|---|---|---|
| | $ED_{50}$ i.p. | Percent ptosis inhit. @ 20 mg/kg i.p. | $ED_{50}$ s.c. | Percent writhing inhib. @ 10 mg/kg s.c. |
| 2-(3-Phenyl-2,3- | 3.03[a] | | | 49[b] |

TABLE 1-continued

| | TBZ | | PQW | |
|---|---|---|---|---|
| | ED$_{50}$ i.p. | Percent ptosis inhit. @ 20 mg/kg i.p. | ED$_{50}$ s.c. | Percent writhing inhib. @ 10 mg/kg s.c. |
| dihydrobenzofuran-3-yl)-N,N—dimethylethylamine oxalate | | | | |
| 2-(3-Phenyl-2,3-dihydrobenzofuran-3-yl)-N—cyano-N—methylethylamine | | 20 | | 59 |
| 2-(3-Phenyl-2,3-dihydrobenzofuran-3-yl)-N—(2,2,2-trichloroethoxycarbonyl)-N—methylethylamine | | 6 | | |
| 2-(3-Phenyl-2,3-dihydrobenzofuran-3-yl)-N—methylethylamine hydrochloride | 4.99$^a$ | | | 53 |
| 2-(3-Phenyl-2,3-dihydrobenzofuran-3-yl)-N—cyclopropylmethyl-N—methylethylamine fumarate | | 22 | 6.27 | |
| 2-(3-Phenyl-2,3-dihydrobenzofuran-3-yl)-N—methyl-N—phenethylethylamine fumarate | | 17 | 20 | |
| 2-(3-Phenyl-2,3-dihydrobenzofuran-3-yl)-N—(2-cyanoethyl)-N—methylethylamine oxalate | | 21 | | 33$^b$ |
| 3-(3-Phenyl-2,3-dihydrobenzofuran-3-yl)-N,N—dimethylpropylamine oxalate | | 37 | | 59$^c$ |
| 3-(3-Phenyl-2,3-dihydrobenzofuran-3-yl)-N—(2,2,2-trichloroethoxycarbonyl)-N—methylpropylamine | | | | 32 |
| 3-(3-Phenyl-2,3-dihydrobenzofuran-3-yl)-N—methylpropylamine hydrochloride | 13.68 | | | 54 |
| 3-(3-Phenyl-2,3-dihydrobenzofuran-3-yl)-N—methyl-N—phenethylpropylamine oxalate | | 0 | | 46 |
| 3-(3-Phenyl-2,3-dihydrobenzofuran-3-yl)-N—cyclopropylmethyl-N—methylpropylamine oxalate | | 10 | | 48 |
| 3-(3-Phenyl-5-chloro-2,3-dihydrobenzofuran-3-yl)-N,N—dimethylpropylamine oxalate | | 15 | | 38$^b$ |
| 3-[3-(4-Tolyl)-2,3-dihydrobenzofuran-3-yl]-N,N—dimethylethylamine fumarate | | 20 | | 61 |
| 3-[3-(2-Tolyl)-2,3-dihydrobenzofuran-3-yl]-N,N—dimethylethylamine fumarate | | 10 | | 34 |
| 3-[3-(2-Fluorophenyl)-2,3-dihydrobenzofuran-3-yl]-N,N—dimethylethylamine fumarate | | 60 | | 35 | a: determined by oral administration
b: at 20 mg/kg
c: at 25 mg/kg

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspension may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
2-(3-Phenyl-2,3-dihydrobenzofuran-3-yl)-N,N-dimethylethylamine oxalate;
2-(3-Phenyl-2,3-dihydrobenzofuran-3-yl)-N-cyano-N-methylethylamine;
2-(3-Phenyl-2,3-dihydrobenzofuran-3-yl)-N-(2,2,2-trichloroethoxycarbonyl)-N-methylethylamine;
2-(3-Phenyl-2,3-dihydrobenzofuran-3-yl)-N-methylethylamine hydrochloride
2-(3-Phenyl-2,3-dihydrobenzofuran-3-yl)-N-cyclopropylmethyl-N-methylethylamine fumarate;
2-(3-Phenyl-2,3-dihydrobenzofuran-3-yl)-N-methyl-N-phenethylethylamine fumarate;
2-(3-Phenyl-2,3-dihydrobenzofuran-3-yl)-N-(2-cyanoethyl)-N-methylethylamine oxalate;
3-(3-Phenyl-2,3-dihydrobenzofuran-3-yl)-N,N-dimethylpropylamine oxalate;
3-(3-Phenyl-2,3-dihydrobenzofuran-3-yl)-N-(2,2,2-trichloroethoxycarbonyl)-N-methylpropylamine;
3-(3-Phenyl-2,3-dihydrobenzofuran-3-yl)-N-methylpropylamine hydrochloride;
3-(3-Phenyl-2,3-dihydrobenzofuran-3-yl)-N-methyl-N-phenethylpropylamine oxalate;
3-(3-Phenyl-2,3-dihydrobenzofuran-3-yl)-N-cyclopropylmethyl-N-methylpropylamine oxalate;
3-(3-Phenyl-5-chloro-2,3-dihydrobenzofuran-3-yl)-N,N-dimethylpropylamine oxalate;
3-[3-(4-Tolyl)-2,3-dihydrobenzofuran-3-yl]-N,N-dimethylethylamine fumarate;
3-[3-(2-Tolyl)-2,3-dihydrobenzofuran-3-yl]-N,N-dimethylethylamine fumarate;
3-[3-(2-Fluorophenyl)-2,3-dihydrobenzofuran-3-yl]-N,N-dimethylethylamine hydrochloride;
alpha-(2-Methoxyphenyl)phenylacetonitrile;
4-Dimethylamino-2-(2-methoxyphenyl)-2-phenylbutyronitrile oxalate;
5-Dimethylamino-2-(2-methoxyphenyl)-2-phenylvaleronitrile hydrochloride;
alpha-(5-Chloro-2-methoxyphenyl)phenylacetonitrile;
5-Dimethylamino-2-(5-chloro-2-methoxyphenyl)-2-phenylvaleronitrile oxalate;
alpha-(2-Methoxyphenyl)-4-tolylacetonitrile;
alpha-(2-Methoxyphenyl)-2-tolylacetonitrile;
4-Dimethylamino-2-(2-methoxyphenyl)-2-(4-tolyl)butyronitrile maleate;
4-Dimethylamino-2-(2-methoxyphenyl)-2-(2-tolyl)butyronitrile maleate;
alpha-(2-Methoxyphenyl)-2-fluorophenylacetonitrile;
4-Dimethylamino-2-(2-fluorophenyl)-2-(2-methoxyphenyl)butyronitrile fumarate;
4-Dimethylamino-2-(2-hydroxyphenyl)-2-phenylbutanol hydrochloride;
5-Dimethylamino-2-(2-hydroxyphenyl)-2-phenylpentanol oxalate;
5-Dimethylamino-2-(5-Chloro-2-hydroxyphenyl)-2-phenylpentanol oxalate;
4-Dimethylamino-2-(2-hydroxyphenyl)-2-(2-tolyl)-butanol hydrochloride;
4-Dimethylamino-2-(2-fluorophenyl)-2-(2-hydroxyphenyl)butanol hemifumarate; and 4-Dimethylamino-2-(2-hydroxyphenyl)-2-(4-tolyl)butanol hemifumarate.

The following examples are shown for the purpose of illustrating the present invention.

EXAMPLE 1

2-(3-Phenyl-2,3-dihydrobenzofuran-3-yl)-N,N-dimethylethylamine oxalate

To a solution of 14.8 g (52 mmole) 4-dimethylamino-2-(2-hydroxyphenyl)-2-phenylbutanol in 300 ml $CH_2Cl_2$ and 21.5 ml (156 mmole) triethylamine which had been cooled in an ice bath for 20 minutes was added a solution of 6 ml (78 mmole) methanesulfonyl chloride in 50 ml $CH_2Cl_2$. After the mixture was stirred 3 hours at ice bath temperature, it was diluted with 800 ml $CH_2Cl_2$, washed with 10% NaOH solution (2×125 ml) and saturated NaCl solution (125 ml), and dried over $MgSO_4$. Filtration and evaporation gave 14.0 g of a crude oil. A solution of 5 g of this material in 15 ml $CH_2Cl_2$ was added to excess oxalic acid in $Et_2O$. The precipitated solid was recrystallized from ethanol to give 4.2 g (63%) of crystals, m.p. 158°–160°.

ANALYSIS: Calculated for $C_{18}H_{21}NO.C_2H_2O_4$: 67.21%C; 6.49%H; 3.92%N. Found: 66.95%C; 6.49%H; 3.90%N.

EXAMPLE 2

2-(3-Phenyl-2,3-dihydrobenzofuran-3-yl)-N-cyano-N-methylethylamine

A solution of 10.9 g (103 mmole) cyanogen bromide and 23 g (86 mmole) of 2-(3-phenyl-2,3-dihydrobenzofuran-3-yl)-N,N-dimethylethylamine in 500 ml $CHCl_3$ was refluxed for 4 hours. The solvent was evaporated and the resultant oil warmed to reflux in 500 ml water. After cooling, the mixture was extracted with $CH_2Cl_2$ (2×1 liter), and the organics were washed with 1N HOAc (3×1 liter) and dried over $K_2CO_3$. Evaporation gave 20 g of an oil, which was chromatographed on 200 g silica gel using $CH_2Cl_2$ as an eluent to give 11 g of an oil which solidified on standing. Recrystallization from acetone/hexane gave 7.1 g (30%) of crystals, m.p. 88°–92°.

ANALYSIS: Calculated for $C_{18}H_{18}N_2O$: 77.67%C; 6.52%H; 10.07%N. Found: 77.72%C; 6.47%H; 10.04%N.

EXAMPLE 3

2-(3-Phenyl-2,3-dihydrobenzofuran-3-yl)-N-(2,2,2-trichloroethoxycarbonyl)-N-methylethylamine A mixture of 6.0 g (22.5 mole) of 2-(3-phenyl-2,3-dihydrobenzofuran-3-yl)-N,N-dimethylethylamine, 3.72 ml (27 mmole) beta,beta,beta-trichloroethyl chloroformate, 12.4 g (90 mmole) anhydrous $K_2CO_3$, and 100 ml anhydrous $CH_2Cl_2$ was stirred at room temperature overnight. Water was then added to dissolve the inorganics and the layers were separated. The organics were washed with water and dried over $MgSO_4$. Filtration and evaporation gave an oil, which was chromatographed with HPLC using 80% $CH_2Cl_2$/hexane as an eluent to give 6.4 g (66%) of an oil.

ANALYSIS: Calculated for $C_{20}H_{20}Cl_3NO_3$: 54.02%C; 4.70%H; 3.27%N. Found: 54.48%C; 4.73%H; 3.08%N.

EXAMPLE 4

2-(3-Phenyl-2,3-dihydrobenzofuran-3-yl)-N-methylethylamine hydrochloride

Activated zinc (14 g, 215 mmole) was added in several portions to a solution of 22 g (54.4 mmole) of 2-(3-phenyl-2,3-dihydrobenzofuran-3-yl)-N-(2,2,2-trichloroethoxycarbonyl)-N-methylethylamine in 125 ml of glacial acetic acid under $N_2$ while cooling the mixture with a water bath. After 1 hour at room temperature, the reaction mixture was diluted with 600 ml $CH_2Cl_2$ and filtered through celite, and the solids were washed with $CH_2Cl_2$. The combined organics were evaporated to dryness and the resultant oil taken up in 800 ml $CH_2Cl_2$. This was washed wit 50 ml saturated $Na_2CO_3$ and dried over $MgSO_4$. Filtration and evaporation gave 12.9 g of an oil. This oil was converted to its hydrochloride salt in $Et_2O$ and the salt recrystallized from $CH_3CN$ to give 9.1 g (61%) of a solid, m.p. 184°–187°.

ANALYSIS: Calculated for $C_{17}H_{19}NO.HCl$: 70.45%C; 6.96%H; 4.83%N. Found: 70.58%C; 7.04H; 4.75%N.

EXAMPLE 5

2-(3-Phenyl-2,3-dihydrobenzofuran-3-yl)-N-cyclopropylmethyl-N-methylethylamine fumarate A mixture of 4.0 g (15.8 mmole) of 2-(3-phenyl-2,3-dihydrobenzofuran-3-yl)-N-methylethylamine, 1.54 g (17.1 mmole) cyclopropylmethyl chloride, 6.9 g (50.0 mmole) $K_2CO_3$ and 0.2 g KI in 40 ml DMF was warmed to 65° and maintained there for 4 hours. After cooling, the reaction mixture was poured into 400 ml water and extracted with $Et_2O$ (3×200 ml). The combined organics were washed with saturated NaCl solution and dried over $Na_2SO_4$. After filtration, the solution was stirred with several grams of silica gel and decanted. After adding 1.85 g fumaric acid and stirring for 1 hour, 4.2 g of solid was collected. This material was recrystallized from $CH_3CN$ to give 2.2 g (33%) of crystals, m.p. 154°–156°.

ANALYSIS: Calculated for $C_{25}H_{27}NO.C_4H_4O_4$: 73.55%C; 6.60%H; 2.96%N. Found: 73.39%C; 6.52%H; 2.98%N.

EXAMPLE 6

2-(3-Phenyl-2,3-dihydrobenzofuran-3-yl)-N-methyl-N-phenethylethylamine fumarate

A mixture of 4.0 g (15.8 mmole) 2-(3-phenyl-2,3-dihydrobenzofuran-3-yl)-N-methylethylamine, 6.9 g (50.0 mmole) anhydrous $K_2CO_3$, 2.35 ml (17.1 mmole) phenethyl bromide, 0.2 g potassium iodide and 40 ml DMF was warmed to 80° and maintained there for 2 hours. After cooling, the mixture was poured into 400 ml water and extracted with $Et_2O$ (3×250 ml). The combined organics were washed with saturated NaCl solution and dried over $MgSO_4$. The crude product, obtained by filtration and evaporation, was converted to a fumarate salt in $Et_2O$. This was recrystallized from $CH_3CN$ to give 2.5 g (33%) of solid, m.p. 135.5°–138°.

ANALYSIS: Calculated for $C_{25}H_{27}NO.C_4N_4O_4$: 73.55%C; 6.60%H; 2.96%N. Found: 73.39%C; 6.52%H; 2.98%N.

EXAMPLE 7

2-(3-Phenyl-2,3-dihydrobenzofuran-3-yl)-N-(2-cyanoethyl)-N-methylethylamine oxalate Acrylonitrile (1.18 ml, 18 mmole) was added dropwise to 4.0 g (15.8 mmole) of 2-(3-phenyl-2,3-dihydrobenzofuran-3-yl)-N-methylethylamine. The resultant mixture was stirred at room temperature for 1.5 hours and at 75° for 3 hours under $N_2$. The cooled mixture was diluted with 400 ml $Et_2O$ and filtered. The filtrate was treated with oxalic acid/$Et_2O$ and the resultant salt was recrystallized from ethanol to give 3.2 g (50%) of a solid, m.p. dec. greater than 144°.

ANALYSIS: Calculated for $C_{20}H_{22}N_2O.C_2H_2O_4$: 66.65%C; 6.10%H; 7.07%N. Found: 66.26%C; 6.06%H; 6.97%N.

EXAMPLE 8

3-(3-Phenyl-2,3-dihydrobenzofuran-3-yl)-N,N-dimethylpropylamine oxalate

To a solution of 5-dimethylamino-2-(2-hydroxyphenyl)-2-phenylpentanol (15.0 g, 50 mmol) in $CH_2Cl_2$ (300 ml) and $Et_3N$ (21.5 ml, 156 mmol) maintained at 5° was added a solution of methanesulfonyl chloride (6.0 ml, 78 mmol) in $CH_2Cl_2$ (50 ml). After the addition was completed, the reaction mixture was diluted with $CH_2Cl_2$ (200 ml), washed with 5% NaOH solution (1×250 ml) and saturated NaCl solution (1×250 ml), and dried over $Na_2SO_4$. Filtration and evaporation gave 12.4 g of a crude oil. A solution of this crude amine in $CH_2Cl_2$ (50 ml) was added to a stirred solution of anhydrous oxalic acid (6.0 g, 66 mmol) in anhydrous $Et_2O$ (500 ml). The precipitated solid was filtered and recrystallized from ethanol (150 ml) to afford 4.5 g (25%) of platelets, m.p. 140.0°–141.0°.

ANALYSIS: Calculated for $C_{19}H_{23}NO \cdot C_2H_2O_4$: 67.91%C; 6.78%H; 3.77%N. Found: 67.74%C; 6.77%H; 3.71%N.

EXAMPLE 9

3-(3-Phenyl-2,3-dihydrobenzofuran-3-yl)-N-(2,2,2-trichloroethoxycarbonyl)-N-methylpropylamine A mixture of 3-(3-phenyl-2,3-dihydrobenzofuran-3-yl)-N,N-dimethylpropylamine (7.40 g, 26 mmol), anhydrous $K_2CO_3$ (14.3 g, 104 mmol), and $CH_2Cl_2$ (125 ml) was stirred at 5°. A solution of 2,2,2-trichloroethyl chloroformate (4.3 ml, 32 mmol) in $CH_2Cl_2$ (5 ml) was added dropwise over 15 minutes. The reaction mixture was stirred at room temperature for 4 hours. Water was then added to dissolve the inorganic salts and the phases were separated. The organic phase was washed with saturated $NaHCO_3$ and saturated NaCl, dried over $Na_2SO_4$, filtered, and evaporated in vacuo to give 7.6 g of a crude oil. This residue was chromatographed by HPLC using $CH_2Cl_2$/hexane (2:1, by volume) as an eluent to yield 3.5 g (30%) of an oil.

ANALYSIS: Calculated for $C_{21}H_{22}Cl_3NO_3$: 56.96%C; 5.01%H; 3.16%N. Found: 56.72%C; 4.96%H; 3.07%N.

EXAMPLE 10

3-(3-Phenyl-2,3-dihydrobenzofuran-3-yl)-N-methylpropylamine hydrochloride

Activated zinc (33.5 g, 516 mmol) was added in several portions to a solution of 3-(3-phenyl-2,3-dihydrobenzofuran-3-yl)-N-(2,2,2-trichloroethoxycarbonyl)-N-methylpropylamine (57 g, 129 mmol) in glacial HOAc (300 ml) while cooling the mixture with a water bath. After stirring 3 hours at room temperature, the reaction mixture was diluted with $CH_2Cl_2$ (500 ml), filtered, and the solids washed with $CH_2Cl_2$ (200 ml). The combined organics were concentrated in vacuo and the residue (63 g) was dissolved in $CH_2Cl_2$ (500 ml). This solution was washed with 5% NaOH (1×400 ml) and saturated $NaHCO_3$ (2×500 ml), dried over $Na_2SO_4$, filtered, and evaporated to afford 26 g (74%) of a crude amine. The amine (3.0 g) was converted to its hydrochloride salt in $Et_2O$ and recrystallized from $CH_3CN$ to yield 2.4 g (52%) of a solid, m.p. 180.0°–181.5°.

ANALYSIS: Calculated for $C_{18}N_{21}NO \cdot HCl$: 71.16%C; 7.30%H; 4.61%N. Found: 71.45%C; 7.34%H; 4.50%N.

EXAMPLE 11

3-(3-Phenyl-2,3-dihydrobenzofuran-3-yl)-N-methyl-N-phenethylpropylamine oxalate

A mixture of 3-(3-phenyl-2,3-dihydrobenzofuran-3-yl)-N-methylpropylamine (6.0 g, 22.4 mmol), anhydrous $K_2CO_3$ (6.9 g, 50 mmol), KI (0.3 g), and phenethyl bromide (3.3 ml, 24 mmol) in DMF (100 ml) was warmed to 80° and maintained there for 4 hours. After cooling, the reaction mixture was poured into ice-water (500 ml) and extracted with $Et_2O$ (3×250 ml). The combined organics were washed with saturated aqueous NaCl, dried over $Na_2SO_4$, and evaporated to afford 7.7 g of a crude amine. The crude product (3.0 g) was chromatographed on $SiO_2$ (0–2% MeOH/$CH_2Cl_2$) to give 2.2 g of pure amine. A solution of the amine in $CH_2Cl_2$ (15 ml) was added to a stirred solution of anhydrous oxalic acid (0.8 g, 8.8 mol) in anhydrous $Et_2O$ (350 ml). The precipitated salt was filtered and recrystallized from boiling EtOAc (150 ml), washed with $Et_2O$ to yield 2.1 g (52%) of salt, m.p. 124°–126°.

ANALYSIS: Calculated for $C_{26}H_{29}NO \cdot C_2H_2O_4$: 72.86%C; 6.77%H; 3.03%N. Found: 73.01%C; 6.72%H; 3.05%N.

EXAMPLE 12

3-(3-Phenyl-2,3-dihydrobenzofuran-3-yl)-N-cyclopropylmethyl-N-methylpropylamine oxalate Cyclopropanecarboxylic acid chloride (3.15 g, 30 mmol) was added dropwise to a solution of 3-(3-phenyl-2,3-dihydrobenzofuran-3-yl)-N-methylpropylamine (6.6 g, 25 mmol) and pyridine (2.8 g, 35 mmol) in $CH_2Cl_2$ (100 ml) at room temperature and the mixture was stirred overnight. The reaction mixture was washed with 5% HCl (2×100 ml), stirred with 5% NaOH (150 ml) for 1 hour, washed with saturated NaCl, dried over $Na_2SO_4$, filtered, and concentrated in vacuo to give 8.2 g of an oily amide (99% by GC).

A solution of the amide (8.2 g, 24 mmol) in THF (30 ml) was added dropwise to a stirred suspension of $LiAlH_4$ (0.93 g, 24 mmol) in THF (85 ml) at room temperature. The reaction mixture was stirred 1 hour, quenched with saturated $NH_4Cl$ (100 ml), and the phases were separated. The organic phase was evaporated in vacuo and the crude amine dissolved in EtOAc (150 ml), washed with 10% $Na_2CO_3$ (2×75 ml) and saturated NaCl (1×75 ml), dried over $Na_2SO_4$, filtered and concentrated in vacuo to give 7.0 g of the amine. A solution of the amine in $Et_2O$ (50 ml) was added dropwise to a stirred solution of anhydrous oxalic acid (2.1 g, 23 mmol) in $Et_2O$ (900 ml). The precipitated salt was filtered and recrystallized from a boiling EtOAc/MeOH (300:40 ml) solution to yield 5.7 g (55%) of a solid, m.p. 147°–148°.

ANALYSIS: Calculated for $C_{22}H_{27}NO \cdot C_2H_2O_4$: 70.05%C; 7.10%H; 3.40%N. Found: 69.98%C; 7.05%H; 3.35%N.

EXAMPLE 13

3-(3-Phenyl-5-chloro-2,3-dihydrobenzofuran-3-yl)-N,N-dimethylpropylamine oxalate To a solution of 5-dimethylamino-2-(5-chloro-2-hydroxyphenyl)-2-phenylpentanol (22.5 g, 68 mmol) in $CH_2Cl_2$ (400 ml) and $Et_3N$ (18.8 ml, 136 mmol) maintained at 5° was added methanesulfonyl chloride (7.8 ml, 102 mmol). The reaction mixture was stirred 2 hours, washed with 5% NaOH (1×250 ml), water and saturated NaCl, and dried over $Na_2SO_4$. Filtration and evaporation gave 20.5 g of a crude residue which was chromatographed by HPLC (2% MeOH:$CH_2Cl_2$) to yield 4.8 g of the amine. A solution of the amine (4.8 g) in $CH_2Cl_2$ (50 ml) was added to a stirred solution of anhydrous oxalic acid (1.6 g, 18 mmol) in $Et_2O$ (300 ml). The precipitated salt (4.8 g) was filtered and recrystallized from MeCN (100 ml) to yield 3.9 g (14%) of crystals, m.p. 163°–164°.

ANALYSIS: Calculated for $C_{19}H_{22}ClNO·C_2H_2O_4$: 62.14%C; 5.97%H; 3.45%N. Found: 62.46%C; 5.94%H; 3.33%N.

EXAMPLE 14

3-[3-(4-Tolyl)-2,3-dihydrobenzofuran-3-yl]-N,N-dimethylethylamine fumarate

To a solution of 4-dimethylamino-2-(2-hydroxyphenyl)-2-(4-tolyl)butanol (18 g, 60 mmol) in $CH_2Cl_2$ (400 ml) and $Et_3N$ (14.5 ml, 105 mmol) maintained at 0° was added methanesulfonyl chloride (6.9 ml, 90 mmol). The reaction mixture was stirred 2 hours, and then stirred with 5% NaOH (100 ml) for 3 hours. The organic layer was separated, washed with water and saturated NaCl, and dried over $Na_2SO_4$. Filtration and evaporation gave 11.3 g of a crude residue, which was chromatographed by HPLC (3.5% $MeOH/CH_2Cl_2$) to yield 4.9 g of an amine. A solution of the amine (4.9 g, 17.5 mmol) in $CH_2Cl_2$ (50 ml) was added to a stirred solution of fumaric acid (3.3 g, 28 mmol) in 15% ethanol/ether (350 ml). The precipitated salt (7.7 g) was filtered and recrystallized from MeCN (140 ml) to yield 6.8 g (29%) of flakes, m.p. 138°–140°.

ANALYSIS: Calculated for $C_{19}H_{23}NO·C_4H_4O_4$: 69.49%C; 6.86%H; 3.52%N. Found: 69.92%C; 6.95%H; 3.62%N. A solution of the amine (4.8 g, 15 mmol) in $CH_2Cl_2$ (50 ml) was added to a stirred solution of anhydrous oxalic acid (1.6 g, 18 mmol) in $Et_2O$ (300 ml). The precipitated salt (4.8 g) was filtered and recrystallized from MeCN (100 ml) to yield 3.9 g (14%) of crystals, m.p. 163°–164°.

ANALYSIS: Calculated for $C_{19}H_{22}ClNO·C_2H_2O_4$: 62.14%C; 5.97%H; 3.45%N. Found: 62.46%C; 5.94%H; 3.33%N.

EXAMPLE 14

3-[3-(4-Tolyl)-2,3-dihydrobenzofuran-3-yl]-N,N-dimethylethylamine fumarate

To a solution of 4-dimethylamino-2-(2-hydroxyphenyl)-2-(4-tolyl)butanol (18 g, 60 mmol) in $CH_2Cl_2$ (400 ml) and $Et_3N$ (14.5 ml, 105 mmol) maintained at 0° was added methanesulfonyl chloride (6.9 ml, 90 mmol). The reaction mixture was stirred 2 hours, and then stirred with 5% NaOH (100 ml) for 3 hours. The organic layer was separated, washed with water and saturated NaCl, and dried over $Na_2SO_4$. Filtration and evaporation gave 11.3 g of a crude residue, which was chromatographed by HPLC (3.5% $MeOH/CH_2Cl_2$) to yield 4.9 g of an amine. A solution of the amine (4.9 g, 17.5 mmol) in $CH_2Cl_2$ (50 ml) was added to a stirred solution of fumaric acid (3.3 g, 28 mmol) in 15% ethanol/ether (350 ml). The precipitated salt (7.7 g) was filtered and recrystallized from MeCN (140 ml) to yield 6.8 mg (29%) of flakes, m.p. 138°–140°.

ANALYSIS: Calculated for $C_{19}H_{23}NO·C_4H_4O_4$: 69.49%C; 6.86%H; 3.52%N. Found: 69.92%C; 6.95%H; 3.62%N.

EXAMPLE 15

3-[3-(2-Fluorophenyl)-2,3-dihydrobenzofuran-3-yl]-N,N-dimethylethylamine hydrochloride To a solution of 4-dimethylamino-2-(2-hydroxyphenyl)-2-(2-tolyl)-butanol (36 g, 120 mmol) in $CH_2Cl_2$ (500 ml) and $Et_3N$ (25 ml, 180 mmol) maintained at 0° was added methanesulfonyl chloride (11.6 ml, 150 mmol). The reaction mixture was warmed to room temperature and stirred overnight. The mixture was washed with $H_2O$ (2×300 ml), 10% $Na_2CO_3$ (2×200 ml) and saturated NaCl, dried over $Na_2SO_4$, and stirred with silica gel (10 g). Filtration and evaporation gave 17.5 g (52%) of the amine. A solution of the amine (16.5 g, 59 mmol) in $CH_2Cl_2$ (100 ml) was added to a stirred solution of fumaric acid (8.0 g, 69 mmol) in 10% ethanol/ether (1100 ml). The precipitated salt (20 g) was filtered and dried. The crude fumarate (3.9 g) was recrystallized from MeCN (450 ml) to yield 3.1 g (35%) of flakes, m.p. 188°–190°.

ANALYSIS: Calculated for $C_{19}H_{23}NO·C_4H_4O_4$: 69.49%C; 6.86%H; 3.52%N. Found: 69.56%C; 6.82%H; 3.71%N.

EXAMPLE 16

3-[3-(2-Fluorophenyl)-2,3-dihydrobenzofuran-3-yl]-N,N-dimethylethylamine hydrochloride To a solution of 4-dimethylamino-2-(2-hydroxyphenyl)-2-(2-fluorophenyl)butanol (10.7 g, 35 mmol) in $CH_2Cl_2$ (200 ml) and $Et_3N$ (7.3 ml, 53 mmol) maintained at 0° was added methanesulfonyl chloride (3.4 ml, 44 mmol). The reaction mixture was warmed to room temperature and stirred overnight. The mixture was washed with $H_2O$ (2×300 ml), 10% $Na_2CO_3$ (2×200 ml) and saturated NaCl, dried over $Na_2SO_4$, and stirred with silica gel (3 g). Filtration and evaporation gave 6.2 g (62%) of the amine. The crude amine (6.2 g) was chromatographed on silica gel eluting with $CH_2Cl_2$ to give 3.2 g of an oil. A solution of the amine (3.2 g, 11.2 mmol) in $CH_2Cl_2$ (15 ml) was added dropwise to an ethereal HCl solution (300 ml). The precipitated salt was recrystallized from MeCN (30 ml) to yield 2.2 g (20%) of crystals, m.p. 211°–213°.

ANALYSIS: Calculated for $C_{18}H_{20}FNO·HCl$: 67.17%C; 6.59%H; 4.35%N. Found: 67.13%C; 6.48%H; 4.24%N.

EXAMPLE 17 alpha-(2-Methoxyphenyl)phenylacetonitrile

To a solution of 30 g (0.125 mole) alpha-(2-methoxyphenyl)-phenylacetaldoxime in 300 ml $CH_2Cl_2$ was added 22 ml (0.15 mole) trifluoroacetic anhydride in 100 ml $CH_2Cl_2$ at 10° over 30 minutes. After stirring at room temperature for 1 hour, the mixture was refluxed for 2 hours. After cooling to room temperature, this was shaken successively with 200 ml 0.2N NaOH, 150 ml saturated $Na_2CO_3$, and 150 ml saturated NaCl solution, and dried over $MgSO_4$. Filtration and evaporation gave 33 g of an oil, which was short-path distilled to give 16 g (56%) of a thick oil which solidified on standing, m.p. 81°–84°. An analytical sample was prepared by one recrystallization from cyclohexane giving needles, m.p. 83°–85°.

ANALYSIS: Calculated for $C_{15}H_{13}NO$: 80.69%C; 5.88%H; 6.27%N. Found: 80.66%C; 5.98%H; 6.25%N.

EXAMPLE 18

4-Dimethylamino-2-(2-methoxyphenyl)-2-phenylbutyronitrile oxalate

To a solution of 6.4 ml (46 mmole) diisopropylamine in 50 ml dry THF maintained at −70° under nitrogen was added 18.2 ml (44 mmole) n-BuLi/hexane (2.42M). The mixture was stirred at −70° for 15 minutes and brought to −30°. A solution of 9.16 g (40 mmole) alpha-(2-methoxyphenyl)-phenylacetonitrile in 50 ml THF was added dropwise and the resultant solution placed in an ice bath for 15 minutes and further stirred at room temperture for 30 minutes. After cooling the mixture to 0°, 11 ml (92 mmole) freshly distilled dimethylaminoethyl chloride was added. The mixture was stirred at room temperature for 15 minutes, then warmed to reflux and maintained there for 1.5 hours. The reaction was quenched with 5 ml water and the volatiles evaporated in vacuo. The residue was taken up in 1 liter $CH_2Cl_2$, washed with water (2×200 ml), and dried over $MgSO_4$. Filtration and evaporation gave an oil, which was taken up in a minimum amount of $CHCl_3$ and then added to a solution of oxalic acid in $Et_2O$. The precipitated salt was collected on a filter, yielding 10.8 g (68%) of a solid, m.p. 175°–178°. An analytical sample was prepared by recrystallization from EtOH, m.p. 177°–179°.

ANALYSIS: Calculated for $C_{19}H_{22}N_2O.C_2H_2O_4$: 65.61%C; 6.29%H; 7.29%N. Found: 65.37%C; 6.33%H; 7.24%N.

EXAMPLE 19

5-Dimethylamino-2-(2-methoxyphenyl)-2-phenyl-valeronitrile hydrochloride

To a solution of diisopropylamine (6.4 ml, 46 mmol) in anhydrous THF (50 ml) maintained at −70° under nitrogen was added n-BuLi/hexane (2.2M, 20 ml, 44 mmol). The solution was stirred at −70° for 15 minutes and brought to −30° C. A solution of alpha-(2-methoxyphenyl)-phenylacetonitrile (9.16 g, 40 mmol) in THF (50 ml) was added dropwise and the resultant solution was allowed to warm to 20° and stirred for 0.5 hour. Distilled 3-dimethylaminopropyl chloride (11.2 g, 92 mmol) was added dropwise and the mixture was refluxed 16 hours. The reaction mixture was cooled and quenched with $H_2O$ (5 ml), the volatiles were evaporated in vacuo and the residue was dissolved in dichloromethane (300 ml) and washed with $H_2O$ (3×100 ml) until the pH of the aqueous phase became 8. The organic solution was dried over $Na_2SO_4$, filtered, and evaporated in vacuo. The residue was dissolved in diethyl ether (300 ml) and saturated with gaseous HCl. The crude precipitated salt (10.4 g, 84%) was collected and dried. Analytically pure material (5.2 g, 38%) was obtained by recrystallization from acetonitrile, m.p. 194.0°–195.5°.

Analysis: Calculated for $C_{20}H_{24}N_2O.HCl$: 69.65%C; 7.34%H; 8.12%N. Found: 69.59%C; 7.29%H; 8.25%N.

EXAMPLE 20

5-Chloro-2-methoxy-alpha-phenylbenzeneacetonitrile

To a solution of o-anisaldehyde (136 g, 1.0 mole) in DMF (1000 ml) was added N-chlorosuccinimide (147 g, 1.10 mole). The reaction mixture was stirred 20 hours at 60°, cooled, poured into ice-water, and extracted with $Et_2O$. The solvent was removed in vacuo to yield 172 g of crystals. Recrystallization from cyclohexane (800 ml) gave 137 g (80%) of 5-chloro-2-methoxybenzaldehyde, m.p. 77°–79°.

A Grignard reagent was prepared by reacting bromobenzene (126 g, 0.8 mole) with Mg (22 g, 0.9 mole) in anhydrous $Et_2O$ (500 ml). A solution of said aldehyde (68 g, 0.4 mole) in $Et_2O$ (700 ml) was added to the $C_6H_5MgBr$ solution at a rate fast enough to maintain reflux. The reaction mixture was quenched with saturated $NH_4Cl$. The organic layer was separated, washed with water and saturated $NaHCO_3$, dried ($Na_2SO_4$) and reduced in vacuo to yield 99 g (99%) of 5-chloro-2-methoxy-alphaphenyl-benzylalcohol which solidified upon standing.

To a solution of said alcohol (99 g, 0.4 mole) and pyridine (40 g, 0.5 mole) in $CHCl_3$ (1000 ml) was added $SOCl_2$ (52 g, 0.44 mol) fast enough to maintain reflux. The reaction mixture was cooled and quenched with water. The organic phase was washed with 5% HCl and saturated $NaHCO_3$, dried over $Na_2SO_4$, and reduced in vacuo to yield 109 g of a crude oil, which deposited crystals upon standing. Decantation of the oil left 75 g (69%) of crystalline alpha,5-dichloro-2-methoxy-alpha-phenyltoluene.

To a solution of the above product (15 g, 56 mmol) in dry MeCN (250 ml) was added AgCN (10 g, 75 mmol). The reaction mixture was refluxed 8 hours, filtered, and reduced in vacuo to afford 16 g of an oil which was chromatographed by HPLC using $CH_2Cl_2$/hexane (1:2 by volume) as an eluent, to yield 6 g of 5-chloro-2-methoxy-alpha-phenylbenzeneacetonitrile (90% pure by GC) contaminated with the corresponding isonitrile.

A solution of the chromatographed nitrile in benzene (25 ml) was stirred with 50% $H_2SO_4$ (80 ml) at room temperature for 16 hours. The organic phase was separated, stirred with $Na_2CO_3$, filtered, and reduced in vacuo to give 5 g of the nitrile which was again chromatographed on 80 g $SiO_2$ ($CH_2Cl_2$/hexane, 1:1 by volume) to give an oil (3.5 g) which solidified upon standing. The solid nitrile was recrystallized from hexane (150 ml) to yield 2.7 g (18%) of powder, m.p. 80.0°–81.0°. A yield of 46% was obtained on a larger scale nitrile synthesis.

ANALYSIS: Calculated for $C_{15}H_{12}ClNO$: 69.90%C; 4.70%H; 5.44%N. Found: 70.02%C; 4.81%H; 5.29%N.

EXAMPLE 21

5-Dimethylamino-2-(5-chloro-2-methoxyphenyl)-2-phenylvaleronitrile oxalate

To a solution of diisopropylamine (9.4 ml, 67 mmol) at −70° was added n-BuLi/hexane (2.2M, 29 ml, 64 mmol), and this solution was stirred and warmed to −30°. A solution of 5-chloro-2-methoxy-alpha-phenyl-benzene acetonitrile (15.0 g, 58 mmol) in THF (60 ml) was added dropwise and the resultant mixture was warmed to 5°. Distilled 3-dimethylaminopropyl chloride (14 g, 115 mmol) was added and the mixture refluxed 20 hours. The reaction mixture was cooled and quenched with $H_2O$ (5 ml) and the volatiles were evaporated in vacuo. The resultant residue was dissolved in $CH_2Cl_2$ (350 ml), washed with $H_2O$ (200 ml) and saturated NaCl, dried over $Na_2SO_4$, filtered, and reduced in vacuo. This residue (21 g) was chromatographed by HPLC (5% MeOH:$CH_2Cl_2$) to yield 16 g of the amine. A solution of the amine (3.6 g, 10.5 mmol) in $Et_2O$ (50 ml) was added to a stirred solution of anhydrous oxalic acid (1.1 g, 12 mmol) in anhydrous $Et_2O$ (300 ml). The precipitated salt was filtered (3.4 g) and recrystallized from boiling MeCN (80 ml) to yield 2.8 g (40%) of salt, m.p. 183.0°–183.5°.

ANALYSIS: Calculated for $C_{20}H_{23}ClN_2O.C_2H_2O_4$: 61.03%C 5.83%H 6.47%N. Found: 60.89%C 5.59%H 6.41%N.

EXAMPLE 22 alpha-(2-Methoxyphenyl)-4-tolylacetonitrile

A solution of o-anisaldehyde (43 g, 320 mmol) in $Et_2O$ (200 ml) was added dropwise to 4-tolylmagnesium bromide/$Et_2O$ (2M, 380 ml, 760 mmol). The reaction mixture was quenched with 5% HCl (1000 ml) and the organic layer was separated, washed with water and saturated NaHCO$_3$, dried over Na$_2$SO$_4$ and reduced in vacuo to yield 84 g of the alcohol.

To a solution of the crude alcohol (84 g) in CH$_2$Cl$_2$ (400 ml) was added SOCl$_2$ (42 g, 350 mmol). The reaction mixture was refluxed 2 hours, then cooled and the volatiles evaporated in vacuo to yield 79 g of the crude chloride.

To a solution of the chloride (79 g, 320 mmol) in dry MeCN (500 ml) was added AgCN (43 g, 320 mmol). The reaction mixture was refluxed 26 hours, filtered, and reduced in vacuo to afford 79 g of an oil which was chromatographed by HPLC using CH$_2$Cl$_2$/hexane (1:2 by volume) as an eluent to yield 47 g (62%) of an oil.

ANALYSIS: Calculated for C$_{16}$H$_{15}$NO: 80.97%C; 6.38%H; 5.90%N. Found: 81.27%C; 6.43%H; 5.59%N.

EXAMPLE 23 alpha-(2-Methoxyphenyl)-2-tolylacetonitrile

To a solution of o-bromotoluene (300 g, 1.75 mole) in THF (1500 ml) at −60° under N$_2$ was added n-BuLi/hexane (2.5M, 375 ml, 0.94 mole) and this solution was stirred 2 hours. A solution of o-anisaldehyde (119 g, 0.88 mole) in THF (400 ml) was added dropwise over 1 hour. The reaction mixture was left standing at room temperature overnight and thereafter quenched with H$_2$O (20 ml), and the volatiles were evaporated in vacuo. The residue was dissolved in CH$_2$Cl$_2$ (1000 ml), washed with dilute HOAc, H$_2$O and dilute NaHCO$_3$, dried over Na$_2$SO$_4$, filtered, and reduced in vacuo to give 215 g of the crude alcohol.

To a solution of the alcohol (215 g) in CH$_2$Cl$_2$ (1000 ml) was added SOCl$_2$ (115 g, 0.97 mole). The reaction mixture was refluxed 2 hours, then cooled and the volatiles evaporated in vacuo to yield 226 g of the crude chloride.

To a solution of the chloride (226 g) in dry MeCN (1500 ml) was added AgCN (118 g, 0.88 mole). The reaction mixture was refluxed 24 hours, filtered, and reduced in vacuo to afford 227 g of an oil. The nitrile was chromatographed by HPLC (hexane/CH$_2$Cl$_2$, 2:1 by volume) to yield 111 g (53%) of a solid. The nitrile (5.4 g) was then recrystallized from hexane (110 ml) to yield 4.5 g (44%) of crystals, m.p. 95.0°–95.5°.

ANALYSIS: Calculated for C$_{16}$H$_{15}$NO: 80.97%C; 6.38%H; 5.90%N. Found: 80.99%C; 6.56%H; 5.85%N.

EXAMPLE 24

4-Dimethylamino-2-(2-methoxyphenyl)-2-(4-tolyl)-butyronitrile maleate

To a solution of diisopropylamine (28 ml, 200 mmol) in anhydrous THF (1000 ml) at −70° was added n-BuLi/hexane (2.4M, 79 ml, 190 mmol) and this solution was stirred and warmed to −30°. A solution of alpha-(2-methoxyphenyl)-4-tolylacetonitrile (41 g, 173 mmol) in THF (200 ml) was added and the resultant mixture was warmed to 5°. Distilled dimethylaminoethyl chloride (37 g, 346 mmol) was added and the mixture refluxed 24 hours. The reaction mixture was cooled, quenched with H$_2$O (50 ml), and the volatiles evaporated in vacuo. The residue was dissolved in CH$_2$Cl$_2$ (750 ml), washed with H$_2$O and saturated NaCl, dried over Na$_2$SO$_4$, filtered, and reduced in vacuo to afford 64 g of a crude residue. A 20 g portion of the crude residue was chromatographed by HPLC (2.5% MeOH:CH$_2$Cl$_2$) to yield 10.8 g of the amine. A solution of the amine (10.8 g, 35 mmol) in CH$_2$Cl$_2$ (50 ml) was added to a stirred solution of maleic acid (4.5 g, 39 mmol) in Et$_2$O (300 ml). The precipitated salt (14.8 g) was recrystallized from EtOH (170 ml) to yield 12.5 g (55%) of crystals, m.p. 175°–176.5°.

ANALYSIS: Calculated for C$_{20}$H$_{24}$N$_2$O.C$_4$H$_4$O$_4$: 67.90%C; 6.66%H; 6.60%N. Found: 67.63%C; 6.68%H; 6.65%N.

EXAMPLE 25

4-Dimethylamino-2-(2-methoxyphenyl)-2-(2-tolyl)-butyronitrile maleate

To a solution of diisopropylamine (74 ml, 530 mmol) in anhydrous THF (2000 ml) at −70° was added n-BuLi/hexane (2.4M, 210 ml, 506 mmol) and this solution was stirred and warmed to −30°. A solution of alpha-(2-methoxyphenyl)-2-tolylacetonitrile (109 g, 460 mmol) in THF (400 ml) was added and the resultant mixture was warmed to 5°. Distilled dimethylaminoethyl chloride (93 g, 860 mmol) was added and the mixture refluxed 24 hours. The reaction mixture was cooled, quenched with water (50 ml), and the volatiles evaporated in vacuo. The residue was dissolved in CH$_2$Cl$_2$ (1000 ml), washed with water and saturated NaCl, dried over Na$_2$SO$_4$, filtered and reduced in vacuo. A 15 g portion of the crude residue (143 g) was chromatographed by HPLC (3% MeOH/CH$_2$Cl$_2$) to yield 10.8 g of the amine. A solution of the amine (10.8 g, 35 mmol) in Et$_2$O/CH$_2$Cl$_2$ (50 ml, 1:1) was added to a stirred solution of maleic acid (5.8 g, 50 mmol) in Et$_2$O (500 ml). The precipitated salt (15 g) was recrystallized from EtOH (100 ml) to yield 13.4 g (66%) of crystals, m.p. 166°–167.5°.

ANALYSIS: Calculated for C$_{24}$H$_{28}$N$_2$O$_5$: 67.90%C; 6.66%H; 6.60;1 %N. Found: 67.92%C; 6.47%H; 6.43%N.

EXAMPLE 26 alpha-(2-Methoxyphenyl)-2-fluorophenylacetonitrile

To a solution of 2-bromofluorobenzene (371 g, 2.12 mole) in THF (2000 ml) at −60° under N$_2$ was added n-BuLi/hexane (2.4M, 860 ml, 2.1 mole) and this solution stirred 0.5 hour. A solution of o-anisaldehyde (144 g, 1.06 mole) in THF (400 ml) was added dropwise over 1 hour. The reaction mixture was stirred at −60° for 4 hours, then quenched with H$_2$O (50 ml), warmed to room temperature and the volatiles evaporated in vacuo. The residue was dissolved in EtOAc (1000 ml), washed with 5% HCl and H$_2$O, dried over Na$_2$CO$_3$, filtered, and reduced in vacuo to give 264 g of the crude alcohol.

To a solution of the alcohol (264 g) in CH$_2$Cl$_2$ (1500 ml) was added SOCl$_2$ (139 g, 1.17 mole). The reaction mixture was refluxed 3 hours, then cooled and the volatiles evaporated in vacuo to yield 284 g of the crude chloride.

To a solution of the chloride (284 g) in dry MeCN (2000 ml) was added AgCN (1.06 mol, 142 g). The reaction mixture was refluxed 24 hours, filtered, and reduced in vacuo to afford 298 g of an oil. The nitrile was chromatographed by HPLC (hexane/CH$_2$Cl$_2$, 2:1) to yield 120 g (47%) of a solid contaminated with the isonitrile. This was dissolved in CH$_2$Cl$_2$ (600 ml) and stirred with concentrated HCl (150 ml) overnight at room temperature. The organic phase was separated, stirred with Na$_2$CO$_3$, filtered, and reduced in vacuo to give 80 g of the nitrile. This was again chromatographed by HPLC (hexane/CH$_2$Cl$_2$, 2:1) to yield 59 g (23%) of a solid. The nitrile (7 g) was recrystallized from C$_6$H$_{12}$ (70 ml) to yield 4.1 g (14%) of crystals, m.p. 97°–98°.

ANALYSIS: Calculated for C$_{15}$H$_{12}$FNO: 74.67%C; 5.02%H; 5.80%N. Found: 74.85%C; 5.09%H; 5.71%N.

EXAMPLE 27

4-Dimethylamino-2-(2-fluorophenyl)-2-(2-methoxyphenyl)butyronitrile fumarate

To a solution of diisopropylamine (44.5 ml, 317 mmol) in THF (1000 ml) at −70° was added n-BuLi/hexane (1.3M, 234 ml, 304 mmol) and this solution was stirred and warmed to −30°. A solution of alpha-(2-fluorophenyl)-2-methoxyphenylacetonitrile (67 g, 276 mmol) in THF (200 ml) was added and the reaction mixture was warmed to 5°. Distilled dimethylaminoethyl chloride (50 g, 460 mmol) was added and the mixture refluxed 24 hours. The reaction mixture was cooled, quenched with water (50 ml), and the volatiles evaporated in vacuo. The residue was dissolved in CH$_2$Cl$_2$ (1000 ml), washed with water and saturated NaCl, dried over Na$_2$SO$_4$, filtered, and reduced in vacuo. The crude residue (80 g) was chromatographed by HPLC (3% MeOH/CH$_2$Cl$_2$) to yield 70 g (81%) of the amine. A solution of the amine (3.1 g, 10 mmol) in CH$_2$Cl$_2$ (15 ml) was added to a stirred solution of fumaric acid (1.5 g, 13 mmol) in 5% EtOH/Et$_2$O solution (500 ml). The precipitated salt (2.6 g) was recrystallized from EtOAc (125 ml) to yield 2.2 g (42%) of crystals, m.p. 146°–148°.

ANALYSIS: Calculated for C$_{19}$H$_{21}$FN$_2$O.C$_4$H$_4$O$_4$: 64.47%C; 5.89%H; 6.53%N. Found: 64.65%C; 5.77%H; 6.69%N.

EXAMPLE 28

4-Dimethylamino-2-(2-hydroxyphenyl)-2-phenylbutanol hydrochloride

A solution of 28.6 g (102 mmole) 2-(2-oxo-3-phenyl-3-dihydrobenzofuranyl)-N,N-dimethylethylamine in 300 ml anhydrous Et$_2$O was added to 7.74 g (204 mmole) LiAlH$_4$ in 150 ml Et$_2$O at ice bath temperature and this mixture stirred at that temperature for 30 minutes. After further stirring for 2 hours at room temperature, the reaction mixture was quenched with saturated Na$_2$SO$_4$, filtered, and the solids washed with excess EtOAc (4×350 ml). The combined organics were washed with saturated Na$_2$CO$_3$ (300 ml) and saturated NaCl (200 ml), and dried over Na$_2$SO$_4$. Filtration and evaporation gave 28 g of a crude oil which solidified on standing. A solution of 5 g of this material in a minimum amount of CH$_2$Cl$_2$ was added to excess Et$_2$O/HCl. Filtration of the precipitated salt gave 5.5 g of a solid which was recrystallized from EtOH to give 3.2 g (57%) of crystals, m.p. 199°–201°.

ANALYSIS: Calculated for C$_{18}$H$_{23}$NO$_2$.HCl: 67.17%C; 7.52%H. Found: 67.08%C; 7.52%H.

EXAMPLE 29

5-Dimethylamino-2-(2-hydroxyphenyl)-2-phenylpentanol oxalate

A solution of 3-(2-oxo-3-phenyl-3-dihydrobenzofuranyl)-N,N-dimethylpropylamine (103 g, 349 mmol) in anhydrous THF (400 ml) was added to a suspension of LiAlH$_4$ (15.3 g, 384 mmol) in Et$_2$O (300 ml) at ice bath temperature and this mixture stirred for 2 hours. After further stirring 1 hour at room temperature the reaction mixture was quenched with saturated Na$_2$SO$_4$, filtered and the solids washed with EtOAc (4×500 ml). The combined organic phases were washed with saturated Na$_2$CO$_3$ (500 ml) and saturated NaCl (500 ml), and dried over Na$_2$SO$_4$. Filtration and evaporation gave 66 g of a crude oil which solidified on standing. A solution of 40 g of this material in CH$_2$Cl$_2$ (60 ml) was added to a stirred solution of anhydrous oxalic acid (19 g) in anhydrous Et$_2$O (600 ml). Filtration of the precipitated salt gave 43 g of a solid. Recrystallization of the oxalate (6.0 g) from boiling EtOH (300 ml) yielded 4.3 g (38%) of crystals, m.p. 182.0°–182.5°.

ANALYSIS: Calculated for C$_{19}$H$_{25}$NO$_2$.C$_2$H$_2$O$_4$: 64.76%C; 6.99%H; 3.59%N. Found: 64.70%C; 7.02%H; 3.51%N.

EXAMPLE 30

5-Dimethylamino-2-(5-chloro-2-hydroxyphenyl)-2-phenylpentanol oxalate

A solution of 3-(5-chloro-2-oxo-3-phenyl-3-dihydrobenzofuranyl)-N,N-dimethylpropylamine (23 g, 70 mmol) in anhydrous THF (100 ml) was added to a suspension of LiAlH$_4$ (1.7 g, 44 mmol) in THF (200 ml) at 0°. This mixture was stirred 1 hour, quenched with saturated NH$_4$Cl (125 ml) and filtered. The solids were washed with EtOAc (2×100 ml), and the combined organic phase was separated and reduced in vacuo. The crude diolamine was dissolved in EtOAc (350 ml), washed with 5% NaHCO$_3$ and saturated NaCl, dried over Na$_2$SO$_4$, and reduced in vacuo to yield 23 g of a gum. A solution of the diolamine (3.5 g) in EtOAc (50 ml) was added dropwise to a solution of anhydrous oxalic acid (1.5 g) in Et$_2$O (300 ml). Filtration of the precipitated salt gave 3.3 g of a solid, which was recrystallized from a boiling EtOH/MeCN solution (3:2, by volume) to yield 2.5 g (56%) of crystals, m.p. 213.5°–214.5°.

ANALYSIS: Calculated for C$_{19}$H$_{24}$ClNO$_2$.C$_2$H$_2$O$_4$: 59.49%C; 6.19%H; 3.30%N. Found: 59.54%C; 6.23%H; 3.34%N.

EXAMPLE 31

4-Dimethylamino-2-(2-hydroxyphenyl)-2-(2-tolyl)-butanol hydrochloride

A solution of 2-[2-oxo-3-(2-tolyl)-3-dihydrobenzofuranyl]-N,N-dimethylethylamine (90 g, 305 mmol) in anhydrous THF (400 ml) was added to a suspension of LiAlH$_4$ (11.4 g, 300 mmol) in THF (850 ml) at 0°. This mixture was stirred 1 hour, quenched with saturated NH$_4$Cl (200 ml) and the organic phase decanted. The solids were washed with EtOAc (3×300 ml) and decanted. The organic solutions were combined and evaporated in vacuo to give an oil which solidified on cooling. The crude residue was dissolved in CH$_2$Cl$_2$ (500 ml), washed with dilute NH$_4$Cl until the pH became 8, and dried over Na$_2$SO$_4$. A solution of the diolamine (8.4 g) in CH$_2$Cl$_2$ (60 ml) was added dropwise to an ethereal/HCl solution (1200 ml). Filtration of the precipitated salt gave 8.6 g of a solid, which was recrystallized from MeCN (800 ml) to yield 6.7 g (71%) of crystals, m.p. 205°–207°.

ANALYSIS: Calculated for C$_{19}$H$_{25}$NO$_2$.HCl: 67.94%C; 7.82%H; 4.17%N. Found: 67.65%C; 7.88%H; 4.20%N.

EXAMPLE 32

4-Dimethylamino-2-(2-fluorophenyl)-2-(2-hydroxyphenyl)butanol hemifumarate

A solution of 2-[2-oxo-3-(2-fluorophenyl)-3-dihydrobenzofuranyl]-N,N-dimethylethylamine (16.1 g, 54 mmol) in THF (50 ml) was added to a suspension of LiAlH$_4$ (2.1 g, 54 mmol) in THF (300 ml) at 0°. This mixture was stirred 1 hour, quenched with EtOAc (60 ml), then saturated NH$_4$Cl (60 ml) was added. The organic phase was decanted, the solids were washed with EtOAc, and the organic solutions were combined and evaporated. The resultant crude residue was dissolved in EtOAc (300 ml), washed with dilute NH$_4$Cl and saturated NaCl, dried over Na$_2$SO$_4$, filtered, and reduced in vacuo to give 13.9 g (85%) of a gum. A solution of the diolamine (3.2 g, 10.6 mmol) in CH$_2$Cl$_2$ (15 ml) was added to a stirred solution of fumaric acid (1.6 g, 14 mmol) in 10% ethanol/ether (300 ml). The precipitated salt (3.2 g) was filtered and dried. The crude fumarate was recrystallized from 50% EtOH/MeCN (400 ml) to yield 2.15 g (48%) of crystals, m.p. 220°–222°.

ANALYSIS: Calculated for C$_{18}$H$_{22}$FNO$_2$.1/2(C$_4$H$_4$O$_4$): 66.46%C; 6.71%H; 3.87%N. Found: 66.10%C; 6.69%H; 3.81%N.

EXAMPLE 33

4-Dimethylamino-2-(2-hydroxyphenyl)-2-(4-tolyl)-butanol hemifumarate

A solution of 2-[2-oxo-3-(4-tolyl)-3-dihydrobenzofuranyl]-N,N-dimethyethylamine (8.2 g, 28 mmol) in THF (35 ml) was added to a suspension of LiAlH$_4$ (0.7 g, 17.5 mmol) in THF (100 ml) at 0°. The mixture was stirred 1 hour, quenched with saturated NH$_4$Cl (30 ml), and diluted with THF (100 ml). The solids were filtered and washed with EtOAc, and the combined organic solutions were evaporated in vacuo. The crude residue was dissolved in EtOAc (100 ml), washed with water and dilute NaCl, dried over Na$_2$SO$_4$, filtered, and reduced in vacuo to give 6.6 g (78%) of a gum. A solution of the diolamine (6.6 g, 22 mmol) in EtOAc (25 ml) was added to a stirred solution of fumaric acid (2.9 g, 25 mmol) in 10% ethanol/ether (300 ml). The precipitated salt (6.7 g) was filtered and dried. The crude fumarate was recrystallized from MeOH (800 ml) to yield 3.5 g (35%) of needles, m.p. 234°–236°.

ANALYSIS: Calculated for C$_{19}$H$_{25}$NO$_2$.1/2(C$_4$H$_4$O$_4$): 70.55%C; 7.63%H; 3.92%N. Found: 70.56%C; 7.57%H; 3.81%N.

We claim:

1. A compound of the formula

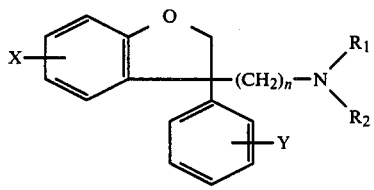

where n is 2 or 3; X and Y are each independently hydrogen, loweralkyl or halogen, R$_1$ is loweralkyl, and R$_2$ is hydrogen, loweralkyl, cyano, beta,beta,beta-trichloroethoxyoxycarbonyl, cyclopropylmethyl, phenethyl or cyanoethyl, with the proviso that when n is 2 and both X and Y are hydrogen, R$_2$ is not hydrogen or loweralkyl, or a pharmaceutically acceptable acid addition salt thereof.

2. The compound as defined in claim 1 where R$_1$ is methyl.

3. The compound as defined in claim 2 where n is 2.

4. The compound as defined in claim 3 where X is hydrogen.

5. The compound as defined in claim 4 where Y is hydrogen.

6. The compound as defined in claim 5 where R$_2$ is cyano, which is 2-(3-phenyl-2,3-dihydrobenzofuran-3-yl)-N-cyano-N-methylethylamine.

7. The compound as defined in claim 5 where R$_2$ is beta,beta,beta-trichloroethoxyoxycarbonyl, which is 2-(3-phenyl-2,3-dihydrobenzofuran-3-yl)-N-(2,2,2-trichloroethoxycarbonyl)-N-methylethylamine.

8. The compound as defined in claim 5 where R$_2$ is cyclopropylmethyl, which is 2-(3-phenyl-2,3-dihydrobenzofuran-3-yl)-N-cyclopropylmethyl-N-methylethylamine.

9. The compound as defined in claim 5 where R$_2$ is phenethyl, which is 2-(3-phenyl-2,3-dihydrobenzofuran-3-yl)-N-methyl-N-phenethylethylamine.

10. The compound as defined in claim 5 where R$_2$ is cyanoethyl, which is 2-(3-phenyl-2,3-dihydrobenzofuran-3-yl)-N-(2-cyanoethyl)-N-methylethylamine.

11. The compound as defined in claim 4 where Y is 4-methyl.

12. The compound as defined in claim 11 where R$_2$ is methyl, which is 3-[3-(4-tolyl)-2,3-dihydrobenzofuran-3-yl]-N,N-dimethylethylamine.

13. The compound as defined in claim 4 where Y is 2-methyl.

14. The compound as defined in claim 13 where R$_2$ is methyl, which is 3-[3-(2-tolyl)-2,3-dihydrobenzofuran-3-yl]-N,N-dimethylethylamine.

15. The compound as defined in claim 4 where Y is 2-fluoro.

16. The compound as defined in claim 15 where R$_2$ is methyl, which is 3-[3-(2-fluorophenyl)-2,3-dihydrobenzofuran-3-yl]-N,N-dimethylethylamine.

17. The compound as defined in claim 2 where n is 3.

18. The compound as defined in claim 17 where X is hydrogen.

19. The compound as defined in claim 18 where Y is hydrogen.

20. The compound as defined in claim 19 where R$_2$ is methyl, which is 3-(3-phenyl-2,3-dihydrobenzofuran-3-yl)-N,N-dimethylpropylamine.

21. The compound as defined in claim 19 where R$_2$ is beta,beta,beta-trichloroethoxycarbonyl, which is 3-(3-phenyl-2,3-dihydrobenzofuran-3-yl)-N-(2,2,2-trichloroethoxycarbonyl)-N-methylpropylamine.

22. The compound as defined in claim 19 where R$_2$ is hydrogen, which is 3-(3-phenyl-2,3-dihydrobenzofuran-3-yl)-N-methylpropylamine.

23. The compound as defined in claim 19 where R$_2$ is phenethyl, which is 3-(3-phenyl-2,3-dihydrobenzofuran-3-yl)-N-methyl-N-phenethylpropylamine.

24. The compound as defined in claim 19 where R$_2$ is cyclopropylmethyl, which is 3-(3-phenyl-2,3-dihydrobenzofuran-3-yl)-N-cyclopropylmethyl-N-methylpropylamine.

25. The compound as defined in claim 17 where X is 5-chloro.

26. The compound as defined in claim 25 where Y is hydrogen.

27. The compound as defined in claim 26 where $R_2$ is methyl, which is 3-(3-phenyl-5-chloro-2,3-dihydrobenzofuran-3-yl)-N,N-dimethylpropylamine.

28. An antidepressant composition comprising an effective depression alleviating amount of a compound of the formula

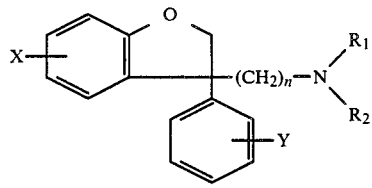

where n is 2 or 3, X and Y are each independently hydrogen, loweralkyl or halogen, $R_1$ is loweralkyl, and $R_2$ is hydrogen, loweralkyl, cyano, beta,beta,beta-trichloroethoxycarbonyl, cyclopropylmethyl, phenethyl or cyanoethyl, with the proviso that when n is 2 and both X and Y are hydrogen, $R_2$ is not hydrogen or loweralkyl, or a pharmaceutically acceptable acid addition salt thereof and a carrier therefor.

29. An analgesic composition comprising an effective pain alleviating amount of a compound of the formula

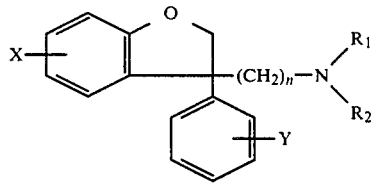

where n is 2 or 3, X and Y are each independently hydrogen, loweralkyl or halogen, $R_1$ is loweralkyl, and $R_2$ is hydrogen, loweralkyl, cyano, beta,beta,beta-trichloroethoxycarbonyl, cyclopropylmethyl, phenethyl or cyanoethyl with the proviso that when n is 2 and both X and Y are hydrogen, $R_2$ is not hydrogen or loweralkyl, or a pharmaceutically acceptable acid addition salt thereof and a carrier therefor.

* * * * *